(12) United States Patent
Hyun et al.

(10) Patent No.: US 9,827,213 B2
(45) Date of Patent: Nov. 28, 2017

(54) ASTRAGALUS MEMBRANACEUS FERMENTATION PRODUCT AND METHOD OF PRODUCING THE SAME

(71) Applicants: CosisBio Co., Ltd., Chungcheongbuk-do (KR); Terry Cho Hyun, Los Angeles, CA (US); Sang-hurn Park, Seoul (KR); Dong-goo Kim, Seongnam-si (KR)

(72) Inventors: Terry Cho Hyun, Los Angeles, CA (US); Sang-hurn Park, Seoul (KR); Dong-goo Kim, Seongnam-si (KR); Ji-young Shin, Chungcheongbuk-do (KR)

(73) Assignee: COSISBIO CO., LTD., Chungcheongbuk-Do (KR)

( * ) Notice: Subject to any disclaimer, the term of this patent is extended or adjusted under 35 U.S.C. 154(b) by 78 days.

(21) Appl. No.: 14/951,421

(22) Filed: Nov. 24, 2015

(65) Prior Publication Data
US 2016/0340703 A1   Nov. 24, 2016

(30) Foreign Application Priority Data
May 20, 2015 (KR) .................. 10-2015-0070630

(51) Int. Cl.
| | |
|---|---|
| *A61K 31/19* | (2006.01) |
| *A61K 31/4965* | (2006.01) |
| *A61K 31/194* | (2006.01) |
| *A61K 31/22* | (2006.01) |
| *A61K 31/015* | (2006.01) |
| *A61K 31/045* | (2006.01) |
| *C12P 1/02* | (2006.01) |
| *C12P 1/04* | (2006.01) |
| *C12R 1/645* | (2006.01) |
| *C12R 1/225* | (2006.01) |

(52) U.S. Cl.
CPC ............ *A61K 31/19* (2013.01); *A61K 31/015* (2013.01); *A61K 31/045* (2013.01); *A61K 31/194* (2013.01); *A61K 31/22* (2013.01); *A61K 31/4965* (2013.01); *C12P 1/02* (2013.01); *C12P 1/04* (2013.01); *C12R 1/225* (2013.01); *C12R 1/645* (2013.01)

(58) Field of Classification Search
None
See application file for complete search history.

(56) References Cited

U.S. PATENT DOCUMENTS

2010/0021426 A1* 1/2010 Wang ................ A61K 31/7056
424/85.4

FOREIGN PATENT DOCUMENTS

KR   10-0906074   6/2009

\* cited by examiner

*Primary Examiner* — Samantha Shterengarts
(74) *Attorney, Agent, or Firm* — Ladas & Parry, LLP

(57) ABSTRACT

Provided are an *astragalus membranaceus* fermentation product and a method of producing the *astragalus membranaceus* fermentation product, in which a lactic acid bacteria starter or a yeast starter proliferated and cultured in a medium is inoculated into a mixture, in which *astragalus membranaceus*, sugar, and water are mixed, to be fermented, and then a pH of a fermentation material obtained by fermenting is measured, and the fermentation material having a pH within a predetermined range is filtered and dried to obtain the *astragalus membranaceus* fermentation product.

6 Claims, 5 Drawing Sheets

ASTRAGALUS MEMBRANACEUS FERMENTATION PRODUCT AND METHOD OF PRODUCING THE SAME

CROSS-REFERENCE TO RELATED APPLICATION

This application claims the benefit of Korean Patent Application No. 10-2015-0070630, filed on May 20, 2015, in the Korean Intellectual Property Office, the disclosure of which is incorporated herein in its entirety by reference.

BACKGROUND

1. Field

One or more exemplary embodiments relate to a method of producing an *astragalus membranaceus* fermentation product obtained by fermenting a mixture including *astragalus membranaceus*, and the *astragalus membranaceus* fermentation product produced by using the method.

2. Description of the Related Art

Due to stresses caused from the rapid changes in life of modern society, work, or personal relationships, more and more people are suffering from diseases such as blood circulation disorders, diabetes, cancer, neuralgia, or arthritis. Also, irregular eating habits and habits of eating fast food frequently caused deficiency of nutrients such as vitamins, fiber, or minerals, increasing the danger of various diseases. Thus, there is a growing interest in *astragalus membranaceus*, which is helpful in supplementing nutrients such as vitamins, fiber, or minerals and preventing various diseases.

*Astragalus membranaceus* is a leguminous perennial herbaceous plant, which contains useful components such as formononetin ($C_{16}H_{12}O_4$), betaine ($C_5H_{11}NO_2$), choline ($C_5H_{15}NO_2$), isoliquiritigenin ($C_{15}H_{12}O_4$), minerals, vitamins, fiber, etc., GABA (γ-Aminobutyric acid) that reduces a blood pressure by working with, saponin having tonic effects, and flavonoide having anticancer effects. Flavonoide, in particular, is a representative component of *astragalus membranaceus*, which is a useful component providing not only anticancer effects but also other helpful functions such as blood sugar control or elimination of oxygen free radicals.

Korean Patent No. 0906074 discloses the manufacture of oriental medicinal healthy drinks based on various medicinal herbs including *astragalus membranaceus*. In most of the related art including *astragalus membranaceus*, the application range of *astragalus membranaceus* is limited in that *astragalus membranaceus* is used just as a traditional medicinal herb or an extract of *astragalus membranaceus* is produced and added to beverages or food. In addition, when *astragalus membranaceus* is boiled with water to drink it as tea or when it is mixed with food to be taken in, useful components of *astragalus membranaceus* which are in the form of polymer may not be easily absorbed into the human body.

SUMMARY

One or more exemplary embodiments include a method of producing an *astragalus membranaceus* fermentation product, in which useful components of *astragalus membranaceus* in the form of polymer are decomposed into low molecules so as to be easily absorbed into the human body, and which also contains various bioactive materials and may be applied to various types of products.

One or more exemplary embodiments include an *astragalus membranaceus* fermentation product produced by using the method.

Additional aspects will be set forth in part in the description which follows and, in part, will be apparent from the description, or may be learned by practice of the presented embodiments.

According to one or more exemplary embodiments, a method of producing an *astragalus membranaceus* fermentation product, includes: culturing a lactic acid bacteria starter or a yeast starter in a medium; inputting *astragalus membranaceus*, sugar, and water to a fermentation tank; fermenting a mixture, in which the *astragalus membranaceus*, the sugar, and the water input to the fermentation tank are mixed, by inoculating the lactic acid bacteria starter or the yeast starter into the mixture; measuring a pH of a fermentation material produced in the fermenting; filtering the fermentation material having a pH measured to be within a predetermined range; and drying the filtered fermentation material. In the culturing of a starter, a MRS medium may be used to cultivate a lactic acid bacteria starter, and a YM medium may be used to cultivate a yeast starter.

The culturing of a starter may include: sterilizing the MRS medium or the YM medium at a high temperature of 120° C. or higher; cooling the sterilized MRS or YM medium to 20° C. to 30° C.; inoculating the lactic acid bacteria starter or the yeast starter into the cooled MRS or YM medium; culturing the lactic acid bacteria starter or the yeast starter inoculated in the inoculating while maintaining the MRS medium or the YM medium at a temperature of 20° C. to 30° C.; and filtering a material cultured by the culturing to extract the lactic acid bacteria starter or the yeast starter. A *Leuconostoc* genus may be used as the lactic acid bacteria starter cultured in the MRS medium, and a *Saccaromyces* genus may be used as the yeast starter cultured in the YM medium.

In the inputting, 10 to 12 parts by weight of the *astragalus membranaceus,* 25 to 31 parts by weight of the sugar, and 10 to 12 parts by weight of the lactic acid bacteria starter or the yeast starter may be input per 100 parts by weight of the water, and the fermenting may be performed by inoculating 10 to 12 parts by weight of the lactic acid bacteria starter or the yeast starter per 100 parts by weight of the water, into the mixture formed by mixing 10 to 12 parts by weight of the *astragalus membranaceus* and 25 to 31 parts by weight of the sugar per 100 parts by weight of the water. In the filtering, the fermentation material having a pH 3.8 or lower measured in the measuring may be filtered using a vacuum filtration method by using a filter paper having small pores of a diameter of about 8 to 10 micrometers.

According to one or more exemplary embodiments, an *astragalus membranaceus* fermentation product may be produced according to the method described above.

BRIEF DESCRIPTION OF THE DRAWINGS

These and/or other aspects will become apparent and more readily appreciated from the following description of the embodiments, taken in conjunction with the accompanying drawings in which.

Figure 1:
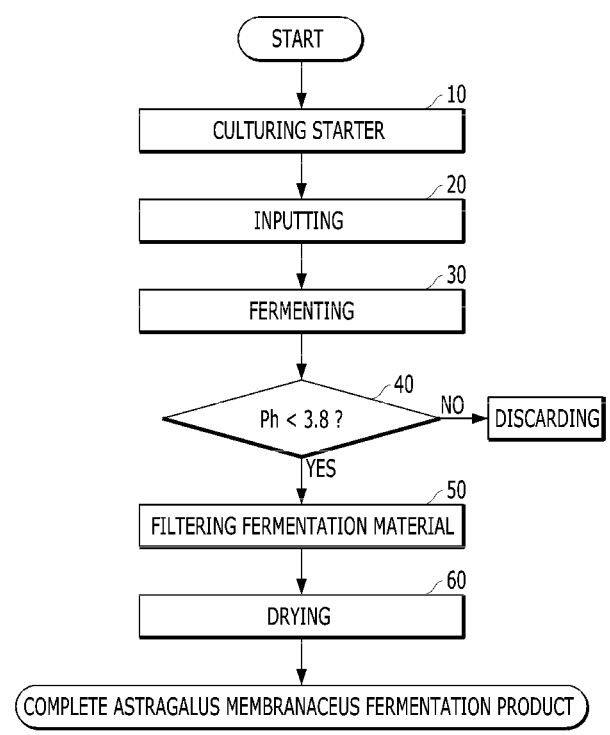
FIG. 1 is a flowchart of a method of producing an *astragalus membranaceus* fermentation product according to an exemplary embodiment, in which operations of FIG. 2 are included.
Figure 3:
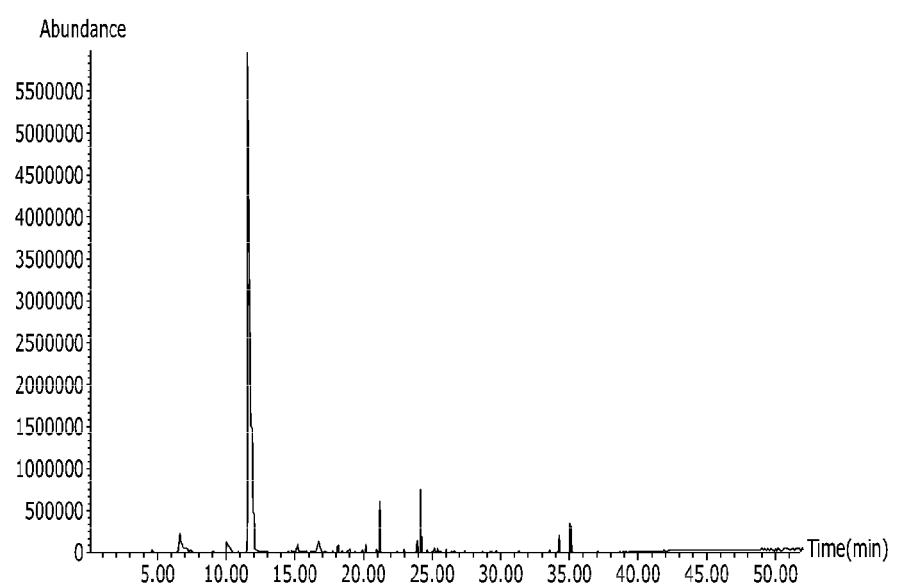
Figure 4:
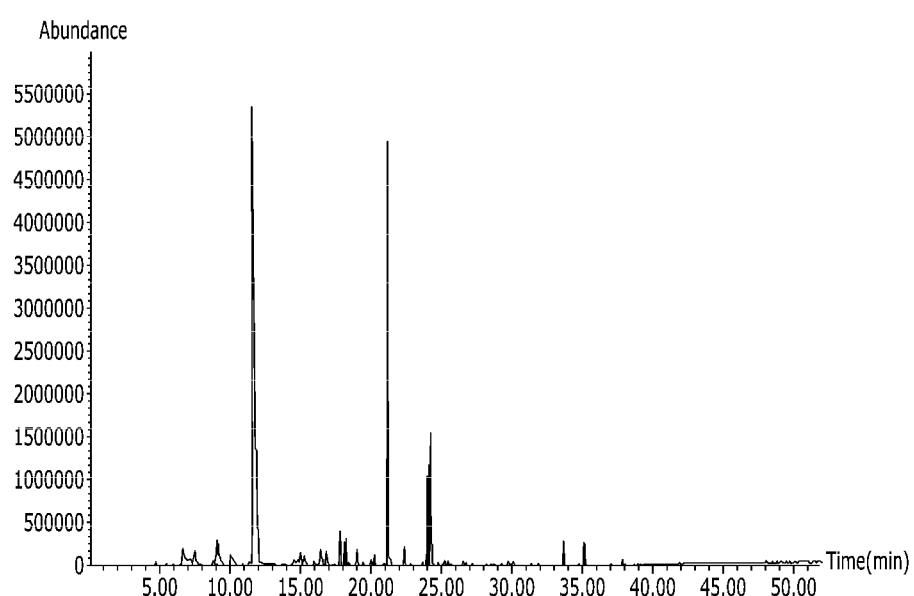
Figure 5:
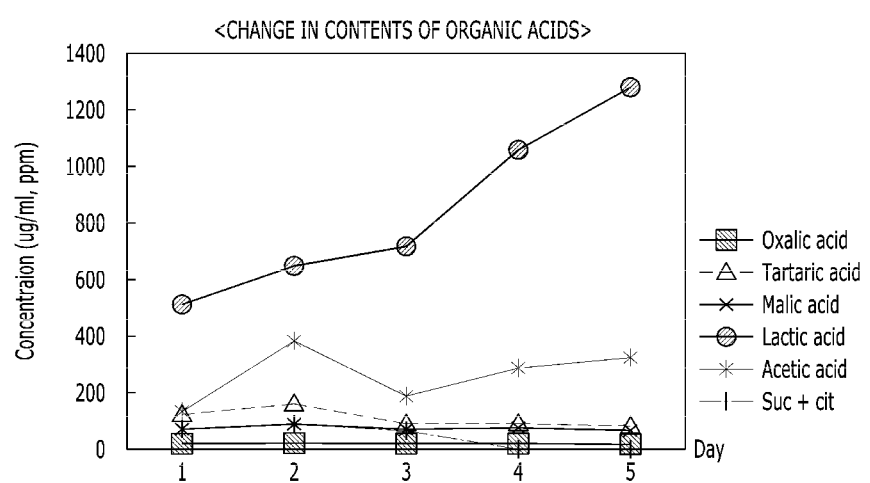

*branaceus* fermentation product according to an exemplary embodiment of the inventive concept;

FIG. 3 is a graph showing a result of gas chromatography-mass spectrometry (GC-MS) analysis of an aroma constituent of a non-fermented mixture produced according to Comparative example 2;

FIG. 4 is a graph showing a result of GC-MS analysis of an aroma constituent of an *astragalus membranaceus* fermentation product produced according to Example 1; and FIG. 5 is a graph showing contents of organic acids of Example 1 produced according to the method illustrated in FIG. 1.

DETAILED DESCRIPTION

Reference will now be made in detail to embodiments, examples of which are illustrated in the accompanying drawings.

The inventive concept is directed to an *astragalus membranaceus* fermentation product produced by generating a fermentation material by inoculating a lactic acid bacteria starter or a yeast starter into a mixture in which *astragalus membranaceus*, sugar, and water are mixed, to be fermented, and filtering and drying the fermentation material. The *astragalus membranaceus* fermentation product was obtained by mixing 10 to 12 parts by weight of *astragalus membranaceus*, 25-31 parts by weight of sugar, and 10 to 12 parts by weight of a starter of lactic acid bacteria or yeast with respect to 100 parts by weight of water, and culturing a mixture of the above-described components by intermittently stirring the mixture and while maintaining the mixture at a temperature of 20 to 30° C. Properties and usage of *astragalus membranaceus*, sugar, lactic acid bacteria or yeast, and water, used to produce the *astragalus membranaceus* fermentation product will be described in detail later.

*Astragalus membranaceus* is a seed of a medicinal plant used as medicine or as a raw material of medicine, and is a dried product of a root of sweet *sophora flavescens* obtained after peeling away the periderm of sweet *sophora flavescens*. Sweet *sophora flavescens* is a leguminous perennial herbaceous plant. The external color of *astragalus* membranceus is light brown or yellowish brown, and inside thereof is yellowish white and smooth, and is characteristics in its sweet odor. *Astragalus membranaceus* contains useful components such as formononetin ($C_{16}H_{12}O_4$), betaine ($C_6H_{11}NO_2$), choline ($C_5H_{15}NO_2$), isoliquiritigenin ($C_{15}H_{12}O_4$), minerals, vitamins, fiber, etc., GABA (γ-Aminobutyric acid) that generates hypotensive effects, saponin having tonic effects, and flavonoide having anticancer effects.

Flavonoide refers to a plant pigment having a $C_6$—$C_3$—$C_6$ carbon skeleton. Examples of flavonoide include flavones, flavanones, isoflavones, antochlores, antocyanes, and catechins. Flavonoide is frequently contained in leafs, roots, flowers, and stems of plants, and in red grapes. Flavonoide kills cancer cells and suppresses new blood vessels, and increases immunity to provide anticancer effects against cancer cells, and reduces blood sugar rates and is thus useful for patients with high blood sugar, and prevents the effects of oxygen free radicals to thereby prevent chronic degenerative diseases such as cancer or cardiovascular disorders. In particular, quercetin ($C_{15}H_{10}O_7$) which is one kind of flavonoide stops proliferation of cancer cells and kills the cancer cells.

In addition, flavonoide removes oxygen free radicals by forming a heavy metal and a chileate compound. Oxygen free radicals are oxygen having a great oxidation force, which are made in various metabolic processes as oxygen absorbed into the human body is used in an oxidation process, and attack living tissues and generates damages to cells. Thus, oxygen free radicals may be the cause of diseases such as cancer, hardening of the arteries, diabetes, or stroke. Such oxygen free radicals may be removed by using flavonoide to thereby prevent and cure various diseases. Moreover, *astragalus membranaceus* contains elements of twenty or more kinds such as magnesium (Mg), iron (Fe), manganese (Mn), tin (Zn), copper (Cu), rubidium (Rb), molybdenum (Mo), chromium (Cr), and selenium (Se) in very small amounts. Selenium (Se), in particular, prevents damages to cells and performs an antioxidant function, and the effect of selenium (Se) is about 500 times higher than that of vitamin E.

The *astragalus membranaceus* fermentation product produced according to the method of the inventive concept includes useful components which are included in *astragalus membranaceus* and in the form of polymer, such as flavonoide, and decomposed to low molecules. Thus, the useful components may be more easily absorbed into the human body than when *astragalus membranaceus* is boiled with water to drink it as tea or when it is mixed with food. Accordingly, an efficiency of preventing or curing various diseases may be increased.

In addition, fiber of *astragalus membranaceus* is used as food for culturing lactic acid bacteria or yeast, and the lactic acid bacteria or yeast that is grown by eating such fiber discharges various organic acids as a product of metabolic activity. An organic acid refers to an organic compound having acidity, such as citric acid, malic acid, acetic acid, tartaric acid, or succinic acid, and the *astragalus membranaceus* fermentation product produced according to Example 1 of the inventive concept contained a large amount of organic acids such as oxalic acid, tartaric acid, or lactic acid. Such organic acids have in vivo antibacterial activities to kill harmful bacteria and facilitate balance of bacteria in the intestines. In addition, the organic acids may help metabolism to improve physical strength and help overcome fatigue, and also help gastric acid activities to activate the digestive functions. A hydroxy acid among organic acids has the effects of preventing skin aging, reducing or preventing acnes, and preventing pigmentation or the like, and is thus used in cosmetic products.

According to the inventive concept, 10 to 12 parts by weight of *astragalus membranaceus* is used per 100 parts by weight of water. If *astragalus membranaceus* is less than 10 parts by weight per 100 parts by weight of water, useful components contained in *astragalus membranaceus* may not be sufficiently supplied to a fermentation material and desired effects of the *astragalus membranaceus* fermentation product according to the inventive concept may not be obtained. If *astragalus membranaceus* is more than 12 parts by weight, space for inhabitation and propagation of lactic acid bacteria or yeast in a medium may be short due to the volume of the *astragalus membranaceus*, decreasing a proliferation efficiency of the lactic acid bacteria and the yeast and causing insufficient fermentation. An excessive amount of *astragalus membranaceus* compared to amounts of lactic acid bacteria or yeast may not be sufficiently fermented but wasted, thereby causing losses.

Lactic acid bacteria refer to bacteria that decompose sugars such as glucose to generate a lactic acid, and are also called *lactobacillus*. A lactic acid generated by lactic acid fermentation which uses lactic acid bacteria has the property of suppressing growth of disease-causing bacteria and harmful bacteria, and products such as milk products, kimchi, or brewery products are manufactured using this property. Also, lactic acid bacteria is an important bacteria used as medicine for intestinal disorders, which inhabits in the intestines of mammals and suppresses abnormal fermentation due to various germs, and is a facultative anaerobic bacteria. Examples of lactic acid bacteria include genera of *Lactobacillus, Leuconostoc*, and *Streptococcus*.

Fermentation which uses lactic acid bacteria is referred to as lactic acid fermentation. In lactic acid fermentation, sugar is decomposed to form a lactic acid. Lactic acid fermentation is one of the two fermentation methods of living organisms, the other of which is alcoholic fermentation, and fermentation of animal tissues also corresponds to lactic acid fermentation. Microorganisms that go through lactic acid fermentation are mucors such as Rhizopusoryzae and bacteria such as lactic acid bacteria. Examples of other microorganisms going through lactic acid fermentation are hetero lactic acid fermentation bacteria (heterogeneous lactic acid fermentation bacteria) that generate, in addition to lactic acid, byproducts such as ethanol, acetic acid, and carbon dioxide, and some other genera of *Lactobacillus* other than the genera of *Leuconostoc*.

According to Example 1 of the inventive concept, *Leuconostoc mesenteriodes* belong to the genera *Leuconostoc* was used as lactic acid bacteria to conduct fermentation. *Leuconostoc mesenteriodes* used in the inventive concept was obtained by isolating it from kimchi. It is difficult for *Leuconostoc mesenteroides* to grow at pH 4.8 or lower, and *Leuconostoc mesenteroides* has vitality in a temperature range of 21 to 25° C., and thus an appropriate temperature and pH should be maintained.

Yeast is a kind of microorganism used in making bread, beer, or wine, and corresponds to mildew or fungus, and refers to all unicellular organisms that have neither hypha nor a photosynthetic capacity or a movement capacity. Yeast is a eukaryote belonging to true fungi, and has a very small size and is difficult to observe with naked eyes. Yeast decomposes sugar to generate alcohol and carbon dioxide, and is frequently used in producing alcoholic beverages.

Fermentation which uses yeast is referred to as yeast fermentation or alcoholic fermentation. Here, yeast decomposes glucose without oxygen or in the presence of insufficient oxygen to generate ethanol and carbon dioxide. In regard to an *astragalus membranaceus* fermentation product produced according to Example 2 of the inventive concept, fermentation was conducted using *Saccaromyces carlbergensis* belonging to the genus of *Saccaromyces*. *Saccaromyces carlbergensis* has similar physiological properties as *Saccaromyces ceresisiae*.

In a fermentation operation 30, which will be described later, fermentation is performed by inoculating a *leuconostoc* genus starter or *saccromyces* genus starter into a mixture obtained by mixing *astragalus membranaceus*, sugar, and water, so that useful elements which are contained in the *astragalus membranaceus* and are in the form of polymer are converted into low molecules. For example, flavonoide which is contained in *astragalus membranaceus* and is in the form of polymer are converted into to low molecules due to fermentation and is absorbed into the small intestine. The absorbed flavonoide has the effects such as controlling blood sugar or anticancer effects.

Meanwhile, sugar included in a fermented material may be synthesized to dextran in the form of polymer via fermentation. Dextran refers to dietary fiber which is not decomposed by internal digestive enzymes of humans, and is not absorbed into the small intestine due to its large molecular weight. Dextran that is not absorbed into the small intestine is food for beneficial bacteria in the large intestine, thereby facilitating activity of the beneficial bacteria and intestinal activity. In addition, dextran adsorbs unnecessary waste existing in the large intestine to thereby facilitate intestinal activity.

Lactic acid bacteria or yeast used according to the inventive concept is 10 to 12 parts by weight per 100 parts by weight of water. If lactic acid bacteria or yeast is less than 10 parts by weight, an amount of organic acids and various useful components formed as a result of metabolic activity of lactic acid bacteria or yeast may be reduced, and lactic acid bacteria or yeast needed in fermentation may not be sufficiently supplied and fermentation may not be performed properly. If lactic acid bacteria or yeast exceeds 12 parts by weight, an amount of lactic acid bacteria or yeast may be excessive compared to a culture medium, and thus food for culturing may not be enough, and space for inhabitation and propagation of lactic acid bacteria or yeast may be small and fermentation may not be properly conducted. Then an *astragalus membranaceus* fermentation product according to the inventive concept may not be produced.

According to the inventive concept, sugar is used as food for culturing lactic acid bacteria or yeast, and glucose is typically used. Glucose is a monosaccharide that has an important function in the body of a living organism, and widely exists in the biological world. When extricated, glucose exists in a large amount in sweet fruit or honey, and a small amount of glucose is contained in blood, cerebrospinal fluid or lymph fluid of animals.

Sugar used according to the inventive concept is 25 to 31 parts by weight per 100 parts by weight of water. If sugar is less than 25 parts by weight, the sugar is not sufficiently supplied as food for culturing lactic acid bacteria or yeast, and an efficiency of proliferation of lactic acid bacteria or yeast is low and fermentation may not be properly performed. If sugar exceeds 31 parts by weight, osmotic pressure phenomenon may decrease a proliferation efficiency of lactic acid bacteria or yeast and fermentation may not be properly conducted.

According to the inventive concept, all the other component than *astragalus membranaceus*, sugar, and a lactic acid bacteria starter or a yeast starter is water, and water is used as a solvent of raw materials. Water has a high specific heat so that it is involved in adjustment of temperature of homoeothermic animals, and is thus not sensitive to a change of state such as a temperature, and does not react with other materials and is thus suitable to be used as a solvent.

The *astragalus membranaceus* fermentation product according to the inventive concept is produced by mixing 10 to 12 parts by weight of *astragalus membranaceus,* 25 to 31 parts by weight of sugar, and 10 to 12 parts by weight of a lactic acid bacteria starter or a yeast starter, with respect to 100 parts by weight of water, and a mixing ratio of these components is an optimum condition for production of the *astragalus membranaceus* fermentation product according to the inventive concept, and preferred exemplary embodiments will be described below.

Hereinafter, a method of producing an *astragalus membranaceus* fermentation product according to an exemplary embodiment of the inventive concept will be described in detail with reference to the drawings.

Figure 2:
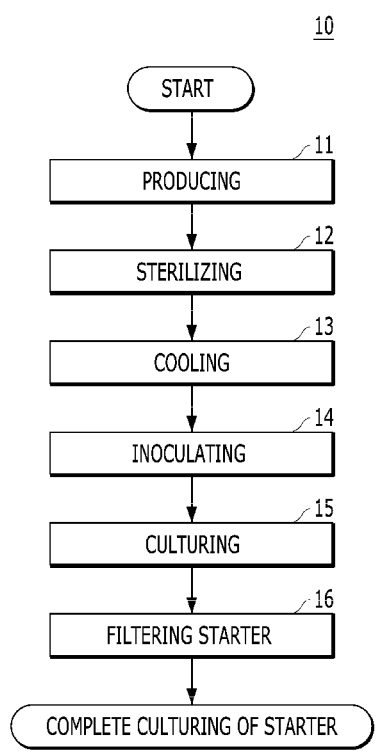
FIG. 2 is a detailed view of a starter culturing operation included in the method of producing an *astragalus mem-*

FIG. 1 is a flowchart of a method of producing an *astragalus membranaceus* fermentation product according to an exemplary embodiment, in which operations of FIG. 2 are included. The method of FIG. 1 includes an operation of a starter culturing operation of FIG. 2, and a starter obtained by using the producing of FIG. 2 is used in the method of FIG. 1, and thus, FIG. 2 will be described first.

FIG. 2 is a detailed view of a starter culturing operation included in the method of producing an *astragalus membranaceus* fermentation product according to an exemplary embodiment of the inventive concept. Referring to FIG. 2, a starter culturing operation 10 includes a preparing operation 11, a sterilizing operation 12, a cooling operation 13, an inoculating operation 14, a culturing operation 15, and a starter filtering operation 16.

In operation 11, when fermentation is performed by using lactic acid bacteria, a MRS medium is prepared, and when fermentation is performed by using yeast, a YM medium is prepared. In detail, materials of a MRS medium facilitate growth of *astragalus membranaceus* and suppress growth of other bacteria competing with *astragalus membranaceus*. In addition, a YM medium is used when culturing yeast, and mainly used when culturing microorganisms that are resistant to acidity. The MRS medium and the YM medium may be manufactured or purchased from the market and used in fermentation.

In operation 12, a MRS medium or a YM medium used in culturing a starter of lactic acid bacteria or a starter of yeast is sterilized for 15 to 30 minutes at a high temperature of about 120° C. or higher. A medium prepared in operation 11 contains various bacteria and pollutant materials, and thus, the pollutant materials and the various bacteria contained in the medium are removed in operation 12. If operation 12 is not performed, unremoved various bacteria may be excessively proliferated in operation 15, which will be described later, and may be hindrance to proliferation of lactic acid bacteria or yeast. Thus, operation 12 of sterilization is necessary.

In operation 13, the sterilized MRS or YM medium is cooled to 20 to 30° C. Operation 12 is performed at a high temperature of 120° C. or higher, and thus, the medium is very hot. The lactic acid bacteria starter or the yeast starter is a microorganism that is sensitive to temperature, and may not be properly proliferated in a high-temperature medium but become extinct. Thus, the medium that has been sterilized is cooled to 20 to 30° C., which is an optimum temperature for culturing starters of lactic acid bacteria or yeast before inoculating the starters of lactic acid bacteria or yeast into the medium. For example, a sterilized and high-temperature medium may be slowly cooled by allowing the medium to stand at a room temperature for 4 to 6 hours or may be quickly cooled by using a low-temperature refrigerating machine. However, if a medium is quickly cooled by using a refrigerating machine, a state of the medium may be changed. Thus, in Examples 1 and 2 of the inventive concept, a medium was slowly cooled by allowing the medium to stand at a room temperature.

In operation 14, the lactic acid bacteria starter or the yeast starter is inoculated into the MRS medium or the YM medium that is cooled in operation 13. In Example 1 of the inventive concept, *Leuconostoc mesenteroides* of *Leuconostoc* genus was inoculated into the MRS medium as an example of the lactic acid bacteria starter, and *saccharomyces carlbergensis* of *saccharomyces* genus was inoculated into the YM medium as an example of the yeast starter, and the lactic acid bacteria stater or the yeast starter described above in an amount corresponding to 10 vol % of a volume of the medium was inoculated.

In operation 15, the lactic acid bacteria starter or the yeast starter inoculated in operation 14 is cultured by maintaining the MRS medium or the YM medium in a temperature range from 20 to 30° C. According to an exemplary embodiment of the inventive concept, the lactic acid bacteria starter or the yeast starter may be proliferated by culturing the lactic acid bacteria starter or the yeast starter for 12 to 24 hours under a condition, in which a temperature of 20 to 30° C., pH 4.2 to 4.8, and acidity of 0.8 to 1.2 are maintained. The lactic acid bacteria starter or the yeast starter proliferated in operation 15 are mixed with *astragalus membranaceus*, sugar, and water in operation 30, which will be described later, to be used in fermentation.

In operation 16, the lactic acid bacteria starter or the yeast starter is obtained by filtering a material cultured in operation 15. For example, the material cultured in operation 15 contains a mixture that includes not only the starters of lactic acid bacteria or yeast but also various byproducts generated due to the medium and the culturing, and these byproducts are removed in operation 16. If the material is used in operation 30 without removing the byproducts generated due to the medium or the culturing, these byproducts may be mixed with *astragalus membranaceus*, sugar, and water, which will be described later, and a mixed medium formed as a result of the mixture may be polluted. Thus, operation 16 is performed for this reason. In operation 16, the material cultured in operation 15 for 12 to 24 hours is filtered using a filter paper having small pores having a size of about 8 to about 10 micrometers. Examples of filtering are vacuum filtration, gravity filtration, and pressure filtration.

As described above, by performing the starter culturing operation 10 including operation 11, operation 12, operation 13, operation 14, operation 15, and operation 16, the starter of lactic acid bacteria or yeast used in the method of producing an *astragalus membranaceus* fermentation product of FIG. 1 may be obtained. The starters of lactic acid bacteria or yeast having a high cfu value with respect to a predetermined weight may be obtained by performing the starter culturing operation 10 which is optimized for starter culturing.

FIG. 1 is a flowchart of a method of producing an *astragalus membranaceus* fermentation product according to an exemplary embodiment, which includes operation of FIG. 2. The method of claim 1 includes the starter culturing operation 10 of FIG. 2, and includes an inputting operation 20, a fermenting operation 30, a measuring operation 40, a filtering operation 50 of filtering a fermented material, and a drying operation 60, used to produce an *astragalus membranaceus* fermentation product according to the inventive concept.

In operation 20, *astragalus membranaceus*, sugar, and water are input to a fermentation tank. According to the present exemplary embodiment, 10 to 12 parts by weight of *astragalus membranaceus* and 25 to 31 parts by weight of sugar are input to the fermentation tank with respect to 100 parts by weight of water in operation 20.

Operation 20 may further include an operation of preparing *astragalus membranaceus*. *Astragalus membranaceus* may be purchased from the market or planted. Such *astragalus membranaceus* contains various byproducts such as soil on its surface, and thus is cleaned, and *astragalus membranaceus* to be used in culturing may be selected among cleaned pieces of *astragalus membranaceus*, and the selected *astragalus membranaceus* may be dehydrated. The above-described *astragalus membranaceus* is sliced to be used, in order to increase an area of reaction thereof with a lactic acid bacteria starter or a yeast starter. In addition, glucose having a sugar content of about 15 Brix is used as sugar input in operation 20.

In operation 30, a mixture, in which *astragalus membranaceus*, sugar, and water input to the fermentation tank, are mixed, are fermented by inoculating the lactic acid bacteria starter or the yeast starter cultured in operation 10 into the mixture. According to the present exemplary embodiment, in operation 30, fermentation is performed by inoculating 10 to 12 parts by weight of the lactic acid bacteria starter or the yeast starter per 100 parts by weight of water, into a mixture formed by mixing 10 to 12 parts by weight of the *astragalus membranaceus* and 25 to 31 parts by weight of the sugar per 100 parts by weight of the water. The fermentation is conducted for 4 to 10 days while maintaining the above-described mixture in a temperature range from about 20° C. to about 30° C. The temperature range of the above-described mixture medium is an optimum temperature condition found out by the inventors of the inventive concept during the manufacture of an *astragalus membranaceus* fermentation product. Thus, a temperature of a mixture is to be maintained at 20 to 30° C. during fermentation.

When *astragalus membranaceus* is boiled with water to drink it as tea or when *astragalus membranaceus* is added to food, the useful components contained in *astragalus membranaceus* and in the form of a polymer are not easily absorbed into the human body. However, according to the inventive concept, the useful components of the *astragalus membranaceus* in the form of a polymer are decomposed into low molecules through the fermentation operation 30 so that the useful components are easily absorbed into the human body. At this time, bioactive substances such as active enzymes, vitamins, minerals, organic acids or the like generated by activity of microorganisms are added, thereby further increasing nutritional contents in the *astragalus membranaceus* fermentation product.

Meanwhile, lactic acid bacteria or yeast used in operation 30 according to the present exemplary embodiment are facultative anaerobic bacteria, and thus no oxygen is additionally supplied by using an air supply device or the like, but oxygen may be supplied by not completely sealing the upper part of the fermentation tank so as to allow ventilation to some extent. In addition, in operation 30, the mixture, into which the lactic acid bacteria starter or the yeast starter is inoculated, is intermittently stirred. However, too frequent stirring may be stressful for the lactic acid bacteria starter or the yeast starter, and thus stirring may be performed a minimum number of times such that the materials input in operation 20 are properly mixed with the lactic acid bacteria or the yeast.

In operation 40, a pH of a fermentation material produced in operation 30 is measured. From at least four days after starting operation 30, a small amount of the fermentation material in the fermentation tank is taken to measure a pH of the fermentation material, and when the measured pH thereof is maintained at 3.8 or lower, operation 50, which will be described later, is performed, and if the pH of the fermentation material is 3.8 or higher, fermentation is further continued up to 10 days after operation 30 is started.

If pH of the fermentation product is 3.8 or higher even after up to 10 days after the start of operation 30, the fermentation product is discarded. If fermentation is continued more than 10 days, insufficient food for culturing may decrease activity of the lactic acid bacteria or yeast and fermentation may not be properly performed. In addition, if fermentation takes place more than 10 days, the mixture in the fermentation tank may be spoiled, and foreign substances may be mixed with the mixture while opening or closing the cover of the fermentation tank to measure pH, and may pollute the fermentation material. When fermentation is performed using yeast, the particular bad smell of the yeast may increase and make it difficult to use the fermentation material, and thus the yeast is discarded.

Meanwhile, pH measurement may be performed by taking a small amount of the fermentation material in the fermentation tank by opening the cover of the fermentation tank and measuring pH of the material. The fermentation material may be taken in a small amount by using a dropping pipette or a syringe.

In operation 50, the fermentation material having a pH value in a predetermined range measured in operation 40 is filtered. The fermentation material formed in operation 30 described above includes lumps of microorganisms, sliced *astragalus membranaceus*, glucose, and various byproducts due to fermentation. In operation 50 according to the present exemplary embodiment, the fermentation material having pH 3.8 or lower is filtered through vacuum filtration in which a filter paper having small pores of a size of about 8 micrometers is used. Accordingly, the lumps of microorganisms, sliced *astragalus membranaceus*, glucose, and various byproducts due to fermentation are removed in operation 50. The *astragalus membranaceus* which has a relatively large size may be removed by using a tweezers or a filter before vacuum filtration.

Here, vacuum filtration refers to a filtration method performed by setting a pressure of a filtering region at a pressure lower than the atmospheric pressure. For vacuum filtration, a Buchner flask, a Buchner funnel, an electrical aspirator, and a filter paper or the like are required. The aspirator generates a vacuum. Vacuum filtration is performed by connecting the aspirator to the Buchner flask, to which a Buchner funnel is connected, and then attaching a filter paper adjusted to a size of the Buchner funnel, to the Buchner funnel. According to the present exemplary embodiment, a filter paper having small pores having a size of about 8 micrometers is used to remove lumps of microorganisms, sliced *astragalus membranaceus*, glucose, and various byproducts due to fermentation so that only the useful components of the fermentation product are left.

In operation 60, the filtered fermentation material is freeze-dried to complete the *astragalus membranaceus* fermentation product. Freeze drying refers to a method of obtaining a dried product by freezing and depressurizing an aqueous solution or a material having a large water content and sublimating ice so as to remove the moisture. In particular, in the case of microorganisms that contain much moisture and are unstable and sensitive to heat, they may be dried typically at a low temperature of about −30° C. to about −10° C. to obtain powder thereof. When operation 60 is performed by freeze-drying, a uniform composition of the *astragalus membranaceus* fermentation product may be maintained, and no additive reaction or pollution is caused, and thus the *astragalus membranaceus* fermentation product may be preserved in its proper state for a long time and the effect thereof may also be maintained for a long time.

The *astragalus membranaceus* fermentation product produced according to operations 10, 20, 30, 40, 50, and 60 of the inventive concept is in the form of powder, and may be taken in as it is or mixed with other useful components and produced as pills for intake. In addition, the *astragalus membranaceus* fermentation product in the form of powder may be used in various fields by mixing the same with dietary supplements, processed food, composites for cosmetic materials or animal feed. The *astragalus membranaceus* fermentation product produced according to the producing method of the inventive concept may be used in other various fields than for the above-described purposes, and the purpose and forms of use thereof are not limited.

Hereinafter, the *astragalus membranaceus* fermentation product will be described in detail with respect to examples, comparative examples, and experimental examples. However, the exemplary embodiments are provided for illustration of the inventive concept only, and the scope of the inventive concept is not limited by the exemplary embodiments.

Example 1

An *astragalus membranaceus* fermentation product was produced as follows according to the above-described exemplary embodiment of the inventive concept. Details that are not described below but provided above may also apply to the present exemplary embodiment. First, a MRS medium was sterilized at a high temperature of about 120° C. for 20 minutes, and was allowed to stand at room temperature for 4 hours to cool the MRS medium to be at a temperature of 20 to 30° C. Then, in the MRS medium maintained at a temperature of 20 to 30° C., *Leuconostoc mesenteroides* was cultured for 24 hours and then filtered to obtain a starter of *Leuconostoc mesenteroides*.

Next, 100 kg of water, 10 kg of *astragalus membranaceus*, 25 kg of glucose, and 10 kg of the starter of *Leuconostoc mesenteroides* cultured in the above-described process were input to a fermentation tank and fermented at 20 to 30° C. for 5 days. The materials in the fermentation tank were stirred every five hours, and stirring was performed for 1 hour each time. Then, pH of a fermentation material generated above was measured, and when the fermentation material has pH 3.8 or lower, the fermentation material was vacuum-filtered using a filter paper having pores of a size of 8 micrometers. Then, the fermentation material was freeze-dried so as to obtain an *astragalus membranaceus* fermentation product.

Example 2

An *astragalus membranaceus* fermentation product was produced as follows according to the above-described exemplary embodiment of the inventive concept. Details that are not described below but provided above may also apply to the present exemplary embodiment. First, a YM medium was sterilized at a high temperature of about 120° C. for 20 minutes, and was allowed to stand at room temperature for 4 hours to cool the YM medium to be at a temperature of 20 to 30° C. Then, in the YM medium maintained at a temperature of 20 to 30° C., *Saccharomyces carbergensis* was cultured for 24 hours and then filtered to obtain a starter of *Saccharomyces carbergensis*.

Next, 100 kg of water, 10 kg of *astragalus membranaceus*, 25 kg of glucose, and 10 kg of the starter of *Saccharomyces carbergensis* cultured in the above-described process were input to a fermentation tank and fermented at 20 to 30° C. for 5 days. The materials in the fermentation tank were stirred every five hours, and the stirring was performed for 1 hour each time. Then, pH of a fermentation material generated above was measured, and when the fermentation material has pH 3.8 or lower, the fermentation material was vacuum-filtered using a filter paper having pores of a size of 8 micrometers. ?) Then, the fermentation material was freeze-dried so as to obtain an *astragalus membranaceus* fermentation product.

Comparative Example 1

100 kg of water and 10 kg of *astragalus membranaceus* were input to a heating tank and heated to boil at about 200° C. for 15 minutes, and then cooled to 60° C. and further heated to boil for about 20 minutes, and then slowly cooled at a room temperature to produce *astragalus membranaceus* tea.

Comparative Example 2

An *astragalus membranaceus* fermentation product according to Comparative example 2 was produced by modifying the conditions of Example 1 as below. First, a MRS medium was sterilized at a high temperature of about 120° C. for 20 minutes, and then was allowed to stand at room temperature for 4 hours to cool the MRS medium to be at a temperature of 20 to 30° C. Then, in the MRS medium maintained at a temperature of 20 to 30° C., *Leuconostoc mesenteroides* was cultured for 24 hours and filtered to obtain a starter of *Leuconostoc mesenteroides*.

Next, 100 kg of water, 10 kg of *astragalus membranaceus*, 25 kg of glucose, and 10 kg of the starter of *Leuconostoc mesenteroides* cultured in the above-described process were input to a fermentation tank to be mixed, thereby producing a non-fermented mixture.

Experimental Example 1

In order to compare and measure anticancer effects of the *astragalus membranaceus* fermentation product produced according to Example 1 and the *astragalus membranaceus* tea produced according to Comparative example 1, an experiment was conducted on mice having a weight of 20 to 25 g and malignant tumor by grouping the mice into three groups and for 15 days. To the mice of Experimental group 1, a mixture of 2 mg of the *astragalus membranaceus* fermentation product according to Example 1 and 0.1 ml of physiological saline solution was orally injected every day. To the mice of Experimental group 2, a mixture of 2 mg of the *astragalus membranaceus* tea according to Comparative example 1 and 0.1 ml of physiological saline solution was orally injected every day. For comparison with the experimental groups, only 0.1 ml of physiologinal saline solution was orally injected to a contrast group. A result of comparing the weight of tumor after 15 days is shown in Table 1.

TABLE 1

| Group | Tumor weight (g) | Reduction rate (%) |
| --- | --- | --- |
| Contrast group (physiological saline solution) | 3.11 ± 0.58 | — |
| Experimental group 1 (*astragalus membranaceus* fermentation product + physiological saline solution) | 2.28 ± 0.59 | 26.69 |
| Experimental group 2 (*astragalus membranaceus* tea + physiological saline solution) | 2.54 ± 0.64 | 18.32 |

As shown in Table 1, the weight of tumor of the experimental groups to which the *astragalus membranaceus* fermentation product or the *astragalus membranaceus* tea was injected was reduced compared to the contrast group to which only physiological saline solution was injected. The tumor weight of Experimental group 1 to which the *astragalus membranaceus* fermentation product was orally injected for 15 days was reduced by about 26.69% compared to the tumor weight of the contrast group which is about 3.11 g. The tumor weight of Experimental group 2 to which the *astragalus membranaceus* tea was orally injected for 15 days was reduced by about 18.32% compared to the tumor weight of the contrast group which is about 3.11 g.

Thus, the tumor weight of Experimental group 1 to which the *astragalus membranaceus* fermentation product was orally injected was more reduced than that of Experimental group 2 to which the *astragalus membranaceus* tea was orally injected. It is determined that the useful components in the form of polymer, contained in *astragalus membranaceus* are decomposed into low molecules through fermentation so as to be easily absorbed into the human body to help cure the disease. That is, this result indicates that the *astragalus membranaceus* fermentation product has anticancer effects.

Experimental Example 2

Aroma constituents of the *astragalus membranaceus* fermentation product produced according to Example 1 and the non-fermented mixture produced according to Comparative example 2 were compared by a gas chromatography-mass spectrometry (GC-MS) analysis. 8 g of the *astragalus membranaceus* fermentation product produced according to Example 1 and 8 g of the non-fermented mixture produced according to Comparative example 2 were taken and a GC-MS analysis was conducted thereon, and an aroma analysis result shown in FIGS. 3 and 4 were obtained. FIG. 3 is a result of GS-MS analysis of the aroma constituent of the non-fermented mixture produced according to Comparative example 2. FIG. 4 is a result of GS-MS analysis of the aroma constituent of the *astragalus membranaceus* fermentation product produced according to Example 1. In graphs according to the GC-MS analysis of FIGS. 3 and 4, a retention time (RT) refers to a period of time from when a sample was injected until the sample was discharged, and a peak area of each component is proportional to a concentration of each component.

TABLE 2

| Retention time (min) | Compound | Area (%) Before fermentation | Area (%) After fermentation |
|---|---|---|---|
| 7.322 | Ethyl acetate | — | 0.210 |
| 11.619 | Toluene | 78.077 | 48.793 |
| 15.840 | Amyl acetate | 0.026 | 0.330 |
| 16.361 | 1,3-dimethyl-benzene | — | 1.597 |
| 17.218 | pyrazine | 0.140 | 0.070 |
| 17.743 | Ethyl hexanoate | 0.203 | 2.007 |
| 18.129 | 1-pentanol | 0.447 | 1.423 |
| 18.429 | 3-octanol | 0.100 | 0.052 |
| 18.88 | methyl pyrazine | 0.257 | 0.060 |
| 21.190 | 1-hexanol | 2.397 | 17.057 |
| 23.893 | 1-octen-3-ol | 0.503 | 2.867 |

The GS-MS analysis showed that the aroma constituent has changed greatly before and after fermentation performed using lactic acid bacteria, and Table 2 shows some of the GC-MS analysis results.

Referring to Table 2, a gas chromatography (GC) peak of toluene was found after 7.322 minutes; toluene had an area of 78.077% before fermentation but an area of 48.793% after fermentation, and thus, an amount of toluene was reduced by about 37% through fermentation. As shown above, from among the compounds shown in Table 2, toluene, pyrazine, and methyl pyrazine were reduced by about 50% or more after fermentation, and ethyl acetate, amyl acetate, 1,3-dimethyl-benzene, ethyl hexanoate, 1-pentanol, 3-octanol, 1-hexanol, and 1-octen-3-ol were remarkably increased after fermentation. In particular, contents of ethyl hexanoate and amyl acetate which are flavoring components added to improve flavor of food are increased, and thus, when the *astragalus membranaceus* fermentation product is used as food, the flavor of food may be improved.

Example 3

Various organic acid components generated during the manufacturing process of the *astragalus membranaceus* fermentation product according to Example 1 by metabolic activity of microorganisms were analyzed by high performance liquid chromatography (HPLC) analysis.

Changes in the contents of organic acids according to the number of days of fermentation are shown in Table 3. The contents of lactic acid and acetic acid were increased as fermentation continues. In detail, the higher content of lactic acid compared to contents of other organic acids indicates that lactic acid bacteria was used in fermentation.

TABLE 3

| Compound (µg/ml) | Number of days of fermentation | | | | |
|---|---|---|---|---|---|
| | 1 | 2 | 4 | 6 | 8 |
| oxalic acid | 17.996 | 21.399 | 18.961 | 19.740 | 16.981 |
| tartaric acid | 133.802 | 166.719 | 94.832 | 96.449 | 87.553 |
| malic acid | 70.171 | 85.735 | 68.755 | 78.125 | 67.763 |
| lactic acid | 510.908 | 653.408 | 719.390 | 1059.587 | 1281.538 |
| acetic acid | 133.066 | 386.328 | 192.384 | 288.192 | 324.020 |
| succinic acid + citric acid | 72.259 | 87.947 | 67.779 | — | — |

The contents of malic acid and oxalic acid were not much changed in amount as fermentation continues, but the content of tartaric acid was reduced as fermentation continues. In addition, succinic acid and citric acid were completely removed from 5 days after fermentation has started. A graph with respect to Table 3 above is shown in FIG. 5.

The inventive concept has been described with reference to the preferred examples, comparative examples, and experimental examples. While this invention has been particularly shown and described with reference to embodiments thereof, it will be understood by those of ordinary skill in the art that the preferred embodiments should be considered in a descriptive sense only and not for purposes of limitation. Therefore, the scope of the inventive concept is defined not by the detailed description of the inventive concept but by the appended claims, and all differences within the scope will be construed as being included in the inventive concept.

According to one or more exemplary embodiments, the *astragalus membranaceus* fermentation product may be produced by fermenting performed by inoculating a lactic acid bacteria starter or a yeast starter into a mixture, in which *astragalus membranaceus*, sugar, and water are mixed, so that useful components in the form of polymer contained in *astragalus membranaceus* are decomposed into low molecules so as to be easily absorbed into the human body, wherein bioactive substances generated by the metabolic activity of lactic acid bacteria or yeast are contained in the *astragalus membranaceus* fermentation product and may supply various nutrients to the human body.

In addition, the effect of *astragalus membranaceus* may be maximized by inoculating 10 to 12 parts by weight of the lactic acid bacteria starter or the yeast starter with respect to 100 parts by weight of the water, into a mixture formed by mixing 10 to 12 parts by weight of *astragalus membrana-*

*ceus* and 25 to 31 parts by weight of sugar with respect to 100 parts by weight of water, so that useful components contained in *astragalus membranaceus* are supplied to the fermentation material as much as possible and *astragalus membranaceus* is fermented sufficiently at the same time.

Also, the powdered *astragalus membranaceus* fermentation product produced according to a method including culturing a starter, inputting materials, fermentation, measurement, filtering, and drying may be taken without any processing or may be mixed with other useful components so as to be used in various fields.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. A method of producing an *astragalus membranaceus* fermentation product, the method comprising:
    culturing a lactic acid bacteria starter or a yeast starter in a medium;
    inputting *astragalus membranaceus*, sugar, and water to a fermentation tank;
    fermenting a mixture, in which the *astragalus membranaceus*, the sugar, and the water input to the fermentation tank are mixed, by inoculating the lactic acid bacteria starter or the yeast starter into the mixture;
    measuring a pH of a fermentation material produced in the fermenting;
    filtering the fermentation material having a pH measured to be within a predetermined range; and
    drying the filtered fermentation material.

2. The method of claim 1, wherein in the culturing of a starter, a MRS medium is used to cultivate a lactic acid bacteria starter, and a YM medium is used to cultivate a yeast starter.

3. The method of claim 2, wherein the culturing of a starter comprises:
    sterilizing the MRS medium or the YM medium at a high temperature of 120° C. or higher;
    cooling the sterilized MRS or YM medium to 20° C. to 30° C.;
    inoculating the lactic acid bacteria starter or the yeast starter into the cooled MRS or YM medium;
    culturing the lactic acid bacteria starter or the yeast starter inoculated in the inoculating while maintaining the MRS medium or the YM medium at a temperature of 20° C. to 30° C.; and
    filtering a material cultured by the culturing to extract the lactic acid bacteria starter or the yeast starter.

4. The method of claim 2, wherein a *Leuconostoc* genus is used as the lactic acid bacteria starter cultured in the MRS medium, and a *Saccaromyces* genus is used as the yeast starter cultured in the YM medium.

5. The method of claim 1, wherein in the inputting, 10 to 12 parts by weight of the *astragalus membranaceus*, 25 to 31 parts by weight of the sugar, and 10 to 12 parts by weight of the lactic acid bacteria starter or the yeast starter are input per 100 parts by weight of the water,
    wherein the fermenting is performed by inoculating 10 to 12 parts by weight of the lactic acid bacteria starter or the yeast starter per 100 parts by weight of water, into the mixture formed by mixing 10 to 12 parts by weight of the *astragalus membranaceus* and 25 to 31 parts by weight of the sugar per 100 parts by weight of the water.

6. The method of claim 1, wherein in the filtering, the fermentation material having a pH 3.8 or lower measured in the measuring is filtered using a vacuum filtration method by using a filter paper having small pores of a diameter of about 8 to 10 micrometers.

* * * * *